US006990375B2

(12) United States Patent
Kloss et al.

(10) Patent No.: US 6,990,375 B2
(45) Date of Patent: Jan. 24, 2006

(54) ADJUSTMENT OF THE BREAKPOINT OF THE RATE RESPONSE CURVE BASED ON MINUTE VENTILATION VALUES

(75) Inventors: Michael Kloss, Magdeburg (DE); Angelo Auricchio, Magdeburg (DE); Veerichetty Kadhiresan, Temecula, CA (US)

(73) Assignee: Cardiac Pacemakers, Inc., Saint Paul, MN (US)

( * ) Notice: Subject to any disclaimer, the term of this patent is extended or adjusted under 35 U.S.C. 154(b) by 513 days.

(21) Appl. No.: 10/087,222

(22) Filed: Mar. 1, 2002

(65) Prior Publication Data

US 2002/0151936 A1 Oct. 17, 2002

Related U.S. Application Data

(60) Provisional application No. 60/273,778, filed on Mar. 2, 2001.

(51) Int. Cl.
*A61N 1/365* (2006.01)
(52) U.S. Cl. .......................................... 607/20; 607/17
(58) Field of Classification Search .................... 607/4, 607/9, 17–20
See application file for complete search history.

(56) References Cited

U.S. PATENT DOCUMENTS

| | | | |
|---|---|---|---|
| 4,719,921 A | 1/1988 | Chirife | 128/419 PG |
| 4,773,401 A | 9/1988 | Citak et al. | 128/419 PG |
| 4,865,036 A | 9/1989 | Chirife | 128/419 D |
| 4,873,980 A | 10/1989 | Schaldach | 128/419 |
| 4,919,137 A | 4/1990 | Schaldach | 128/419 PG |
| 4,926,863 A | 5/1990 | Alt | 128/419 PG |
| 4,940,053 A | 7/1990 | Mann et al. | 128/419 PG |
| 4,945,909 A | 8/1990 | Fearnot et al. | 128/419 PG |
| 5,078,133 A | 1/1992 | Heinz et al. | 128/419 PG |
| 5,154,171 A | 10/1992 | Chirife | 128/419 PG |
| 5,156,147 A | 10/1992 | Warren et al. | 128/419 PG |
| 5,168,869 A | 12/1992 | Chirife | 128/419 PG |
| 5,170,785 A | 12/1992 | Heinz et al. | 128/419 PG |
| 5,174,286 A | 12/1992 | Chirife | 128/419 PG |
| 5,179,949 A | 1/1993 | Chirife | 128/419 PG |
| 5,197,467 A | 3/1993 | Steinhaus et al. | 128/419 PG |
| 5,226,413 A | 7/1993 | Bennett et al. | 128/419 PG |
| 5,303,702 A | 4/1994 | Bonnet et al. | 607/20 |
| 5,376,106 A | 12/1994 | Stahmann et al. | 607/18 |
| 5,423,870 A | 6/1995 | Olive et al. | 607/18 |
| 5,487,753 A | 1/1996 | MacCarter et al. | 607/17 |
| 5,562,711 A | 10/1996 | Yerich et al. | 607/17 |
| 5,645,575 A | 7/1997 | Stangl et al. | 607/17 |
| 5,792,195 A | 8/1998 | Carlson et al. | 607/17 |
| 5,931,858 A | 8/1999 | Kadhiresan et al. | 607/20 |
| 5,974,340 A | 10/1999 | Kadhiresan | 607/18 |
| 6,119,040 A | 9/2000 | Chirife | 607/18 |
| 6,273,856 B1 | 8/2001 | Sun et al. | 600/300 |

(Continued)

OTHER PUBLICATIONS

Soucie, Luc P., et al., "Correlation of the Heart Rate-Minute Ventilation Relationship with Clinical Date: Relevance to Rate-Adaptive Pacing", *PACE, Part I*, vol. 20, Aug. 1997, 1913-1918.

(Continued)

*Primary Examiner*—Robert E. Pezzuto
*Assistant Examiner*—Kristen Mullen
(74) *Attorney, Agent, or Firm*—Schwegman, Lundberg, Woessner & Kluth, P.A.

(57) ABSTRACT

A method and system for operating a rate-adaptive pacemaker utilizing minute ventilation to measure exertion level. The method is applicable to heart failure patients who exhibit an oscillatory minute ventilation pattern.

20 Claims, 4 Drawing Sheets

Fig.4

U.S. PATENT DOCUMENTS

| | | | |
|---|---|---|---|
| 6,411,850 B1 | 6/2002 | Kay et al. | 607/20 |
| 6,490,485 B1 | 12/2002 | Sun et al. | 607/20 |
| 6,509,588 B1 | 1/2003 | O'Phelan et al. | 257/209 |
| 6,519,495 B1 | 2/2003 | Sun et al. | 607/18 |
| 6,522,525 B1 | 2/2003 | O'Phelan et al. | 361/509 |
| 6,571,126 B1 | 5/2003 | O'Phelan et al. | 607/5 |
| 6,674,634 B2 | 1/2004 | O'Phelan et al. | 361/509 |
| 6,684,102 B1 | 1/2004 | O'Phelan et al. | 607/5 |
| 6,687,118 B1 | 2/2004 | O'Phelan et al. | 361/508 |
| 6,699,265 B1 | 3/2004 | O'Phelan et al. | 607/1 |
| 6,709,946 B2 | 3/2004 | O'Phelan et al. | 438/396 |
| 6,823,214 B1 * | 11/2004 | Sun et al. | 607/17 |
| 6,839,593 B1 * | 1/2005 | Sun et al. | 607/17 |

OTHER PUBLICATIONS

Treese, Norbert, et al., "Ventilation and Heart Rate Response During Exercise in Normals: Relevance for Rate Variable Pacing", *PACE*, vol. 16, Aug. 1993, (Aug. 1990), 1693-1700.

Benditt, David G., et al., "Sensor-Triggered, Rate-Variable Cardiac Pacing", *Annals of Internal Medicine*, vol. 107, No. 5, (Nov. 1987), 714-724.

Sun, Weimin, et al., "Improved Rate-Adaptive Therapy With Automatic Limiting of Maximum Pacing Rate", U.S. Appl. No. 09/657,404, filed Sep. 8, 2000, 29 pgs.

Sun, Weimin, et al., "Self-Calibrating Rate-Adaptive Pacemaker", U.S. Appl. No. 09/657,402, filed Sep. 8, 2000, 30 pgs.

Sun, Weimin, et al., "Self-Calibrating Rate-Adaptive Pacemaker", U.S. Appl. No. 10/839,875, filed May 6, 2004, 30 pgs.

Weimin, Sun, et al., "Rate-Adaptive Therapy With Sensor Cross-Checking", U.S. Appl. No. 10/364,129, filed Feb. 10, 2003, 20.

* cited by examiner

ADJUSTMENT OF THE BREAKPOINT OF THE RATE RESPONSE CURVE BASED ON MINUTE VENTILATION VALUES

CROSS-REFERENCE TO RELATED APPLICATION(S)

This application claims the benefit of U.S. Provisional Application Ser. No. 60/273,778, filed Mar. 2, 2001, under 35 U.S.C. 119(e).

FIELD OF THE INVENTION

This invention pertains to apparatus and methods for cardiac rhythm management. In particular, the invention relates to improvements in providing rate-adaptive and/or resynchronization pacing therapy to heart failure patients.

BACKGROUND

Cardiac pacemakers are cardiac rhythm management devices that attempt to compensate for the heart's inability to pace itself adequately in order to meet metabolic demand, termed bradycardia pacing. A pacemaker is an implantable battery-powered electronic device that responds to sensed cardiac events and elapsed time intervals by changing its functional states so as to properly interpret sensed data and deliver pacing pulses to the heart at appropriate times. Additional sensing of physiological data allows some pacemakers to change the rate at which they pace the heart in accordance with some parameter correlated to metabolic demand. Such pacemakers are called rate-adaptive pacemakers.

Heart failure is a clinical syndrome in which an abnormality of cardiac function causes cardiac output to fall below a level adequate to meet the metabolic demand of peripheral tissues and is usually referred to as congestive heart failure (CHF) due to the accompanying venous and pulmonary congestion. CHF can be due to a variety of etiologies with ischemic heart disease being the most common. Some CHF patients suffer from some degree of AV block or are chronotropically deficient such that their cardiac output can be improved with conventional bradycardia pacing. Such pacing, however, may result in some degree of uncoordination in atrial and/or ventricular contractions due to the way in which pacing excitation is spread throughout the myocardium without use of the normal specialized conduction pathways. The resulting diminishment in cardiac output may be significant in a CHF patient whose cardiac output is already compromised. Intraventricular and/or interventricular conduction defects are also commonly found in CHF patients. In order to treat these problems, cardiac rhythm management devices have been developed which provide electrical pacing stimulation to one or more heart chambers in an attempt to improve the coordination of atrial and/or ventricular contractions, termed cardiac resynchronization therapy.

Heart failure patients may be treated with pacemakers that provide rate-adaptive pacing and/or resynchronization therapy. The present invention is concerned with improving the way in which such therapies are delivered to these patients.

SUMMARY OF THE INVENTION

The present invention relates to a cardiac pacemaker in which the presence or absence of oscillatory minute ventilation patterns are detected and used to optimize pacing therapy in heart failure patients. It has been found that patients who are suffering from some degree of heart failure commonly exhibit an oscillatory minute ventilation pattern during rest and at exertion levels up to the anaerobic threshold. Accordingly, in one embodiment, minute ventilation values are measured as a patient's exertion level increases, with the resulting minute ventilation signal filtered to extract the oscillatory component. The oscillatory component is determined to be present if its amplitude is above a specified threshold value. If the oscillatory component falls below the specified threshold value as the patient's exertion level increases, the anaerobic threshold can be assumed to have been reached at that particular exertion level. In order to optimize the operation of a rate-adaptive pacemaker using a dual-slope rate response curve, the breakpoint of the curve is then set to the minute ventilation value at which the oscillatory minute ventilation pattern ceased.

In a rate-adaptive pacemaker using minute ventilation as a measure of exertion level, an oscillatory minute ventilation pattern may cause inappropriate adjustments to be made to the pacing rate. In another embodiment, therefore, a rate-adaptive pacemaker operating in a heart failure patient known to exhibit an oscillatory minute ventilation pattern is programmed to utilize another exertion level sensor to cross-check minute ventilation values before adjusting the pacing rate. For example, an activity level sensor such as an accelerometer can be used to provide a measure of the patient's activity level which is then compared with a minute ventilation reading. Only if the minute ventilation reading and the corresponding activity level measurement match within a specified range is the pacing rate adjusted. In this way, changes in minute ventilation due solely to the oscillatory component are ignored and not allowed to cause inappropriate adjustments to the pacing rate.

It has also been found that the degree to which heart failure patients exhibit an oscillatory minute ventilation pattern correlates with the degree to which their cardiac output is compromised. Measurement of oscillatory minute ventilation patterns can thus be used to monitor the effectiveness of a pacemaker configured to deliver cardiac resynchronization therapy, which therapy has been shown to be beneficial in raising the cardiac output of heart failure patients. In particular embodiments, measurement of the oscillatory component of minute ventilation can either be used to automatically adjust resynchronization pacing parameters or be reported to a clinician via an external programmer so that appropriate therapy modifications can be made.

DETAILED DESCRIPTION

Figure 1:
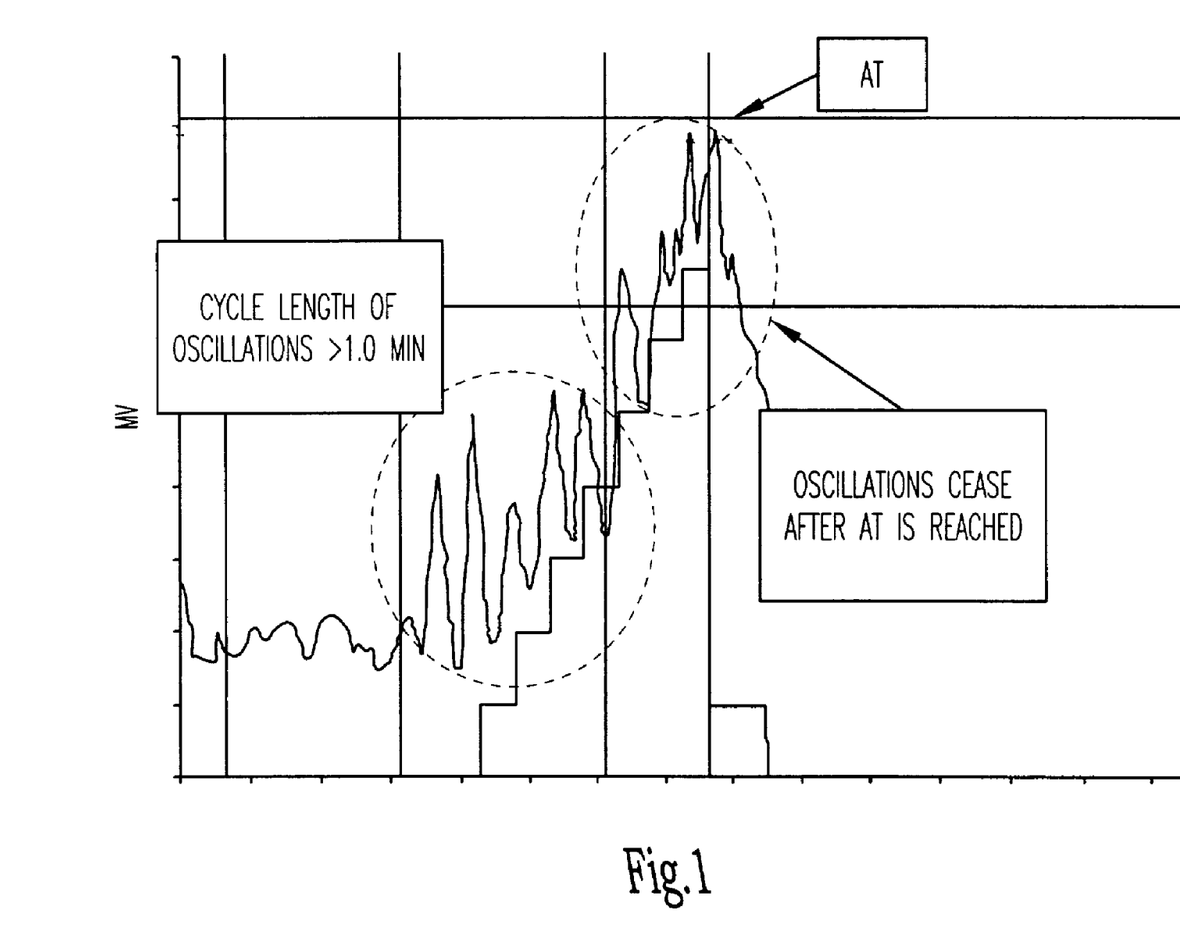
FIG. 1 illustrates an oscillatory minute ventilation pattern.

Based upon cardiopulmonary exercise tests, it has been found that heart failure patients consistently exhibit an oscillatory minute ventilation pattern, with the period of the oscillations typically greater than one minute. It has also been found that the oscillatory pattern occurs at the onset of exercise but disappears once the patient reaches the anaerobic threshold. FIG. 1 illustrates an example of an oscillatory minute ventilation pattern in which minute ventilation MV is plotted against time T as a patient exercises with increasing intensity. As shown in the figure, the oscillations cease when the patient reaches an exertion level corresponding to the anaerobic threshold AT. Additionally, the magnitude of the oscillations decreases when effective therapy is instituted that increases cardiac output, such as ventricular resynchronization therapy. Although the cause of the oscillatory behavior is not known with certainty, it is supposed that neuro-hormonal mechanisms are involved. The present invention relates to a method and apparatus for utilizing detection of an oscillatory minute ventilation pattern in order to optimize rate-adaptive and/or resynchronization pacing in heart failure patients.

1. Bradycardia Pacing

The most common condition for which pacemakers are used is the treatment of bradycardia. Permanent pacing for bradycardia is indicated in patients with symptomatic bradycardia of any type as long as it is likely to be permanent or recurrent and is not associated with a transient condition from which the patient may recover. Atrio-ventricular conduction defects (i.e., AV block) that are fixed or intermittent and sick sinus syndrome represent the most common indications for permanent pacing. Modern pacemakers are typically programmable so that they can operate in any mode which the physical configuration of the device will allow. Such modes define which heart chambers are paced, which chambers are sensed, and the response of the pacemaker to a sensed P wave or R wave (i.e., an atrial or ventricular sense, respectively). A three-letter code is used to designate a pacing mode where the first letter refers to the paced chamber(s), the second letter refers to the sensed chamber(s), and the third letter refers to the response.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate limit interval is then the sum of the atrial escape interval and the atrio-ventricular interval.

2. Rate-Adaptive Pacing

In chronotropically competent patients in need of ventricular pacing, atrial tracking modes such as DDD or VDD are desirable because they allow the pacing to track the physiologically normal atrial rhythm, which causes cardiac output to be responsive to the metabolic needs of the body. Atrial tracking modes are contraindicated, however, in patients prone to atrial fibrillation or flutter or in whom a reliable atrial sense cannot be obtained. In the former case, the ventricles will be paced at too high a rate. Failing to sense an atrial P wave, on the other hand, results in a loss of atrial tracking which can lead to negative hemodynamic effects because the pacemaker then reverts to its minimum ventricular pacing rate. In pacemaker patients who are chronotropically incompetent (e.g., sinus node dysfunction) or in whom atrial-triggered modes such as DDD and VDD are contraindicated, the heart rate is determined solely by the pacemaker in the absence of intrinsic cardiac activity. That heart rate is the lower rate limit or LRL.

Pacing the heart at a fixed rate as determined by the LRL setting of the pacemaker, however, does not allow the heart rate to increase with increased metabolic demand. Cardiac output is determined by two factors, the stroke volume and heart rate, with the latter being the primary determinant. Although stroke volume can be increased during exercise, the resulting increase in cardiac output is usually not sufficient to meet the body's metabolic needs unless the heart rate is also increased. If the heart is paced at a constant rate, as for example by a VVI pacemaker, severe limitations are imposed upon the patient with respect to lifestyle and activities. It is to overcome these limitations and improve the quality of life of such patients that rate-adaptive pacemakers have been developed. Rate-adaptive pacemakers operate so as to vary the lowest rate at which the heart is allowed to beat in accordance with one or more physiological parameters related to metabolic demand.

The body's normal regulatory mechanisms act so as to increase cardiac output when the metabolic rate is increased due to an increased exertion level in order to transport more oxygen and remove more waste products. One way to control the rate of a pacemaker, therefore, is to measure the metabolic rate of the body and vary the pacing rate in accordance with the measurement. Metabolic rate can effectively be directly measured by, for example, sensing blood pH or blood oxygen saturation. Practical problems with implementing pacemakers controlled by such direct measurements, however, have led to the development of pacemakers that are rate-controlled in accordance with physiological variables that are indirectly reflective of the body's metabolic rate such as body temperature, ventilation rate, or minute ventilation. Minute ventilation varies almost linearly with aerobic oxygen consumption during exercise up to the anaerobic threshold and is the physiological variable that is most commonly used in rate-adaptive pacemakers to reflect the exertion level of the patient.

An even more indirect indication of metabolic rate is provided by the measurement of body activity or motion. Body activity is correlated with metabolic demand because such activity requires energy expenditure and hence oxygen consumption. An activity-sensing pacemaker uses a piezoelectric sensor or accelerometer inside the pacemaker case that responds to vibrations or accelerations by producing electrical signals proportional to the patient's level of physical activity.

In such rate-adaptive pacemakers that vary the pacing rate in accordance with a measured exertion level, the control system is generally implemented as an open-loop controller that maps a particular exertion level to one particular target heart rate, termed the sensor-indicated rate. The mapping is accomplished by a rate-response curve which is typically a linear function (i.e., a straight line), but could also be some non-linear function as well such as a dual-slope curve or exponential curve. The rate-response curve is then defined with minimum and maximum target heart rates. A minimum target heart rate for a patient can be ascertained clinically as a heart rate adequate to sustain the patient at rest, while a maximum allowable target heart rate is defined with a formula that depends on the patient's age. The rate-response curve then maps a resting exertion level to the minimum heart rate and maps the maximum exertion level attainable by the patient, termed the maximum exercise capacity, to the maximum allowable heart rate. The responsiveness of the control system, defined as how the target heart rate changes with a given change in exertion level, depends upon the slope of the rate-response curve (or slopes in the case of a dual-slope curve) which is dictated by the defined maximum exercise capacity. An under-responsive pacemaker will unnecessarily limit exercise duration and intensity in the patient because the heart rate will not increase enough to match metabolic demand, while an over-responsive pacemaker can lead to palpitations and patient discomfort.

Figure 2A:
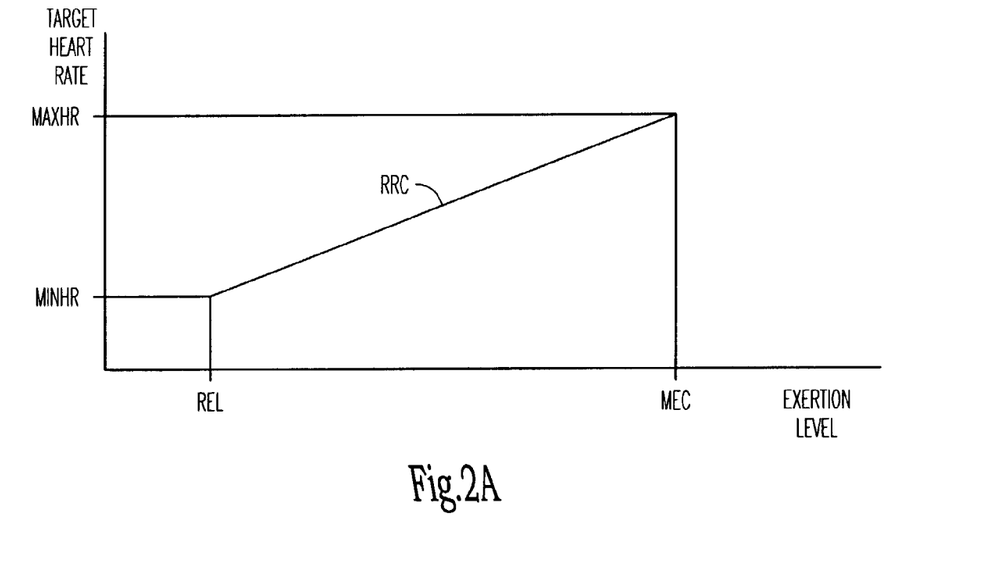
FIGS. 2A and 2B depicts rate-response curves.

The responsiveness of a rate-adaptive pacemaker is controlled in accordance with a rate-response curve RRC such as shown in FIG. 2A. Other embodiments may use a dual-slope curve or a non-linear curve as described below. A change in exertion level as determined from a minute ventilation measurement causes a proportional change in the target heart rate in accordance with the slope of the curve, termed the response factor RF. The target heart rate is then used as a lower rate limit by the pacemaker to pace the heart in accordance with a programmed pacing mode. As shown in the figure, the rate response curve maps a resting exertion level REL to a minimum target rate MinHR which corresponds to the minimum LRL that is to be used by the pacemaker. The maximum target rate MaxHR is the maximum rate at which the pacemaker is allowed to pace the heart and is mapped to by the rate response curve from the maximum exertion level the patient is expected to be able to reach, referred to as the maximum exercise capacity MEC. In the single-slope rate response curve shown in FIG. 2, the response factor RF may then be defined as:

$$RF = (MaxHR - MinHR)/(MEC - REL)$$

Figure 2B:
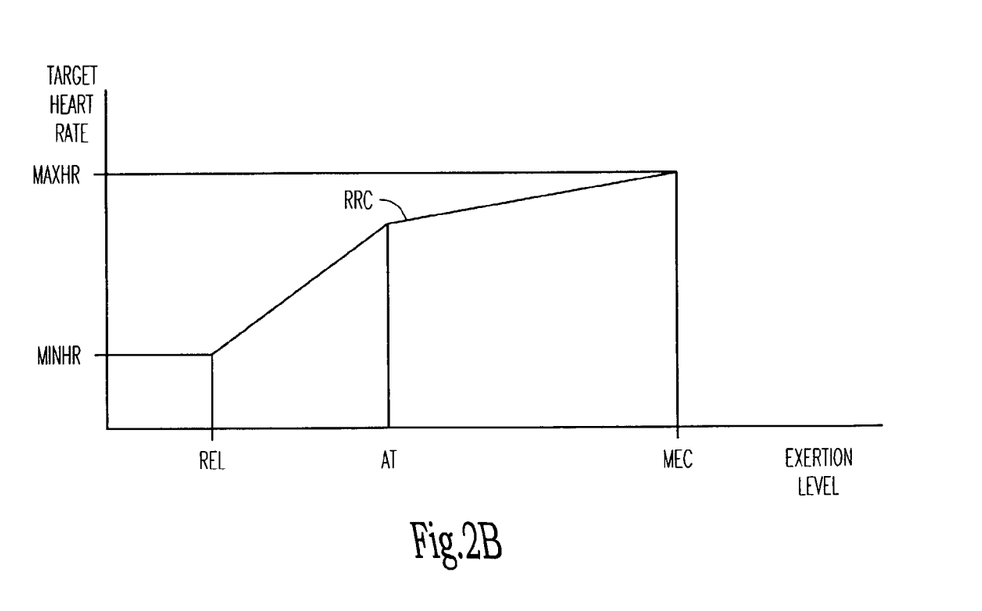
Figure 3:
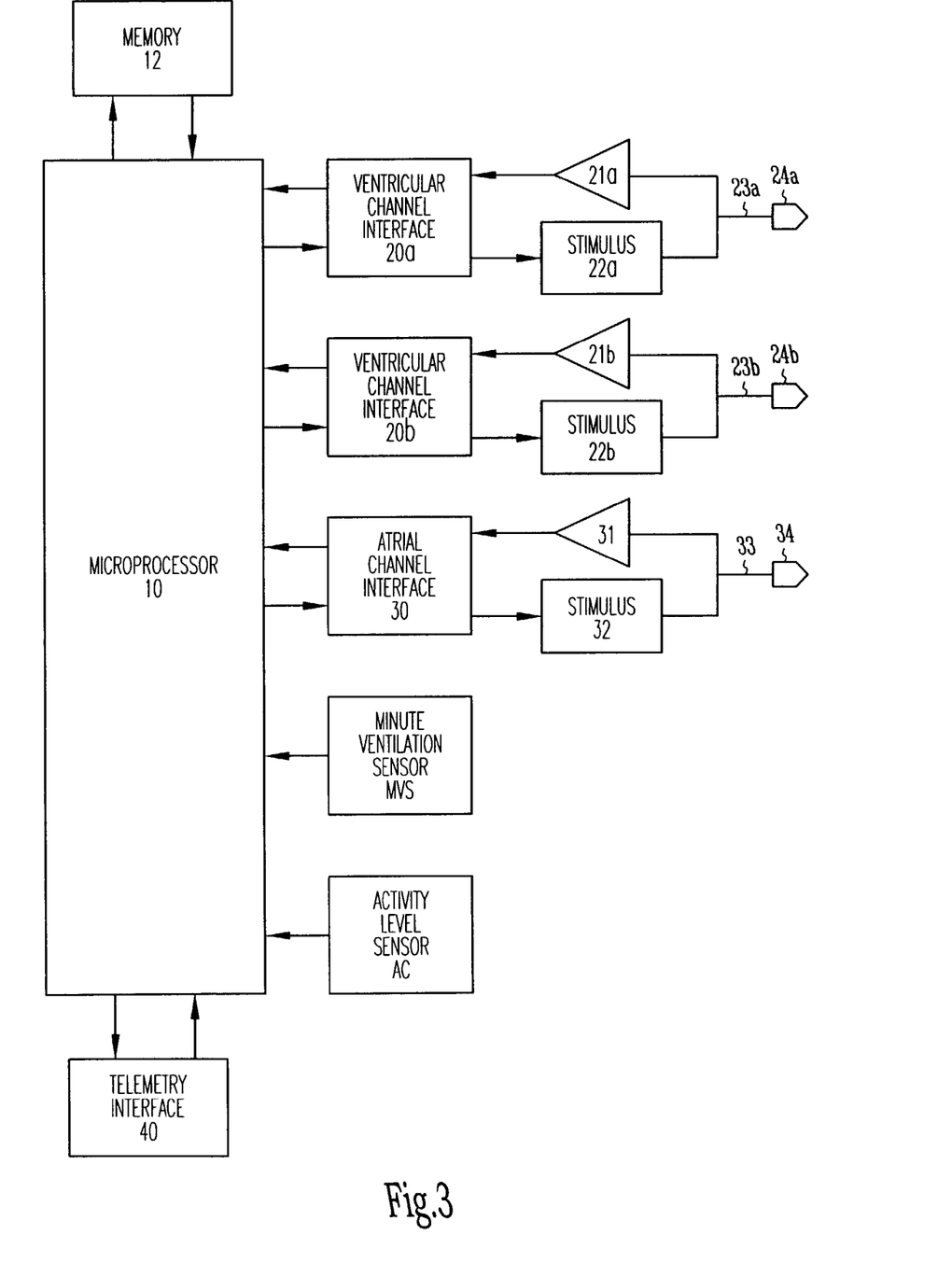
FIG. 3 is a diagram of a rate-adaptive pacemaker.

The responsiveness of the pacemaker can also be controlled in accordance with a dual-slope rate response curve such as shown in FIG. 2B. A change in exertion level EXL (as determined from either minute ventilation or body activity) causes a change in the sensor indicated rate that is proportional to the slope of the response curve. The slope of the rate response curve is designated the initial response factor RF below the heart rate breakpoint HRB, and designated the high rate response factor HRRF above HRB. The heart rate breakpoint HRB ideally should be set to correspond to an exertion level equal to the anaerobic threshold AT of the patient. The anaerobic threshold is the level of exertion above which the concentration of lactic acid produced by anaerobic metabolism starts to build up rapidly in the blood. It thus represents an exertion level at which the body starts to utilize oxygen less efficiently and, along with maximal oxygen consumption, is a useful index of current physical conditioning. The responsiveness of the pacemaker below the anaerobic threshold as defined by RF should be greater than that above the threshold as defined by HRRF so that overpacing above the anaerobic threshold can be avoided.

3. Resynchronization Therapy

Cardiac resynchronization therapy is pacing stimulation applied to one or more heart chambers in a manner that restores or maintains synchronized contractions of the atria and/or ventricles and thereby improves pumping efficiency. Certain patients with conduction abnormalities may experience improved cardiac synchronization with conventional single-chamber or dual-chamber pacing as described above. For example, a patient with left bundle branch block may have a more coordinated contraction of the ventricles with a pace than as a result of an intrinsic contraction. Resynchronization pacing, however, may also involve delivering paces to multiple sites of a heart chamber or pacing both ventricles and/or both atria in accordance with a resynchronization pacing mode as described below. Ventricular resynchronization pacing is useful in treating heart failure because, although not directly ionotropic, resynchronization results in a more coordinated contraction of the ventricles with improved pumping efficiency and increased cardiac output. Resynchronization pacing of the atria may also be beneficial in certain heart failure patients, particularly for preventing the onset of atrial arrhythmias.

One way to deliver resynchronization therapy is to pace a site with a synchronous bradycardia pacing mode and then deliver one or more resynchronization paces to one or more additional pacing sites in a defined time relation to one or more selected sensing and pacing events that either reset escape intervals or trigger paces in the bradycardia pacing mode. One such resynchronization pacing mode may be termed offset resynchronization pacing. In this mode, a first site is paced with a bradycardia mode, and a second site receives a resynchronization pace at an offset interval with respect to the pace delivered to the first site. The offset interval may be zero in order to pace both sites simultaneously, positive in order to pace the first site after the second, or negative to pace the first site before the second. For example, in biventricular resynchronization pacing, one ventricle is paced with a bradycardia mode while the contralateral ventricle receives resynchronization paces at the specified biventricular offset interval. The offset interval would normally be individually specified to optimize cardiac output in a particular patient. Ventricular resynchronization can also be achieved in certain patients by pacing at a single unconventional site, such as the left ventricle instead of the right ventricle. In such a mode, right ventricular senses may be used to trigger left ventricular paces or used to define an escape interval that upon expiration causes delivery of a left ventricular pace.

In a particular implementation of cardiac resynchronization therapy, one atrium and/or one ventricle are designated as rate chambers, and paces are delivered to the rate chambers based upon pacing and sensed intrinsic activity in the chamber in accordance with the bradycardia pacing mode. In a single-chamber bradycardia pacing mode, for example, one of the paired atria or one of the ventricles is designated as the rate chamber. In a dual-chamber bradycardia pacing mode, either the right or left atrium is selected as the atrial rate chamber and either the right or left ventricle is selected as the ventricular rate chamber. The heart rate and the escape intervals for the pacing mode are defined by intervals between sensed and paced events in the rate chambers only. Resynchronization therapy may then be implemented by adding synchronized pacing to the bradycardia pacing mode where paces are delivered to one or more synchronized pacing sites in a defined time relation to one or more selected sensing and pacing events that either reset escape intervals or trigger paces in the bradycardia pacing mode. In bilateral synchronized pacing, which may be either biatrial or biventricular synchronized pacing, the heart chamber contralateral to the rate chamber is designated as a synchronized chamber. For example, the right ventricle may be designated as the rate ventricle and the left ventricle designated as the synchronized ventricle, and the paired atria may be similarly designated. Each synchronized chamber is then paced in a timed relation to a pace or sense occurring in the contralateral rate chamber.

4. Hardware Platform

Pacemakers are typically implanted subcutaneously or submuscularly in a patient's chest and have leads threaded intravenously into the heart to connect the device to electrodes used for sensing and pacing. (As used herein, the term pacemaker should be taken to mean any cardiac rhythm management device with a pacing functionality including an implantable cardioverter/defibrillator that includes a pacemaker.) Leads may also be positioned on the epicardium by various means. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

A particular implementation of a rate-adaptive pacemaker that may also be configured to deliver ventricular resynchronization therapy is shown in FIG. 1. A microprocessor 10 serves as the device controller and communicates with a memory 12 via a bidirectional data bus 13. The memory 12 typically comprises a ROM or RAM for program storage and a RAM for data storage. The controller senses cardiac events through a sensing channel and outputs pacing pulses to the heart via a pacing channel in accordance with a programmed pacing mode. Sensing and/or pacing channels include the leads made up of electrodes on a catheter or wire that connect the pacemaker to the heart. In this embodiment, the pacemaker has atrial sensing and pacing channels comprising electrode 34, lead 33, sensing amplifier 31, pulse generator 32, and an atrial channel interface 30 which communicates bidirectionally with a port of microprocessor 10. The device also has sensing and pacing channels for each ventricle comprising electrodes 24a–b, leads, sensing amplifiers 21a–b, pulse generators 22a–b, and ventricular channel interfaces 20a–b, where "a" and "b" refer to components associated with the left or right ventricle, respectively. For each channel, the same lead and electrode are used for both sensing and pacing. The channel interfaces 20 and 30 may include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. A telemetry interface 40 is also provided for communicating with an external programmer.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The sensing circuitry of the pacemaker detects a chamber sense, either an atrial sense or ventricular sense, when a sense signal (i.e., a voltage sensed by an electrode representing cardiac electrical activity, sometimes called an electrogram signal) generated by a particular channel exceeds a specified intrinsic detection threshold. Pacing algorithms used in particular pacing modes employ such senses to trigger or inhibit pacing. A minute ventilation sensor MVS and an accelerometer AC are employed to sense the minute ventilation and body activity, respectively. The pacemaker uses the sensed minute ventilation and/or the accelerometer signal to adjust the rate at which the pacemaker paces the heart in the absence of a faster intrinsic rhythm. The microprocessor 10 executes programmed instructions that implement various pacing and rate-adaptive algorithms in accordance with parameters that define the pacing mode and pacing configuration, the latter referring to which of the available channels are to be used for sensing and/or pacing. The microprocessor is also programmed to implement the method for adjusting these parameters in accordance with measurements of the minute ventilation oscillations as described below.

5. Optimization of Rate-Adaptive Pacing

Figure 4:
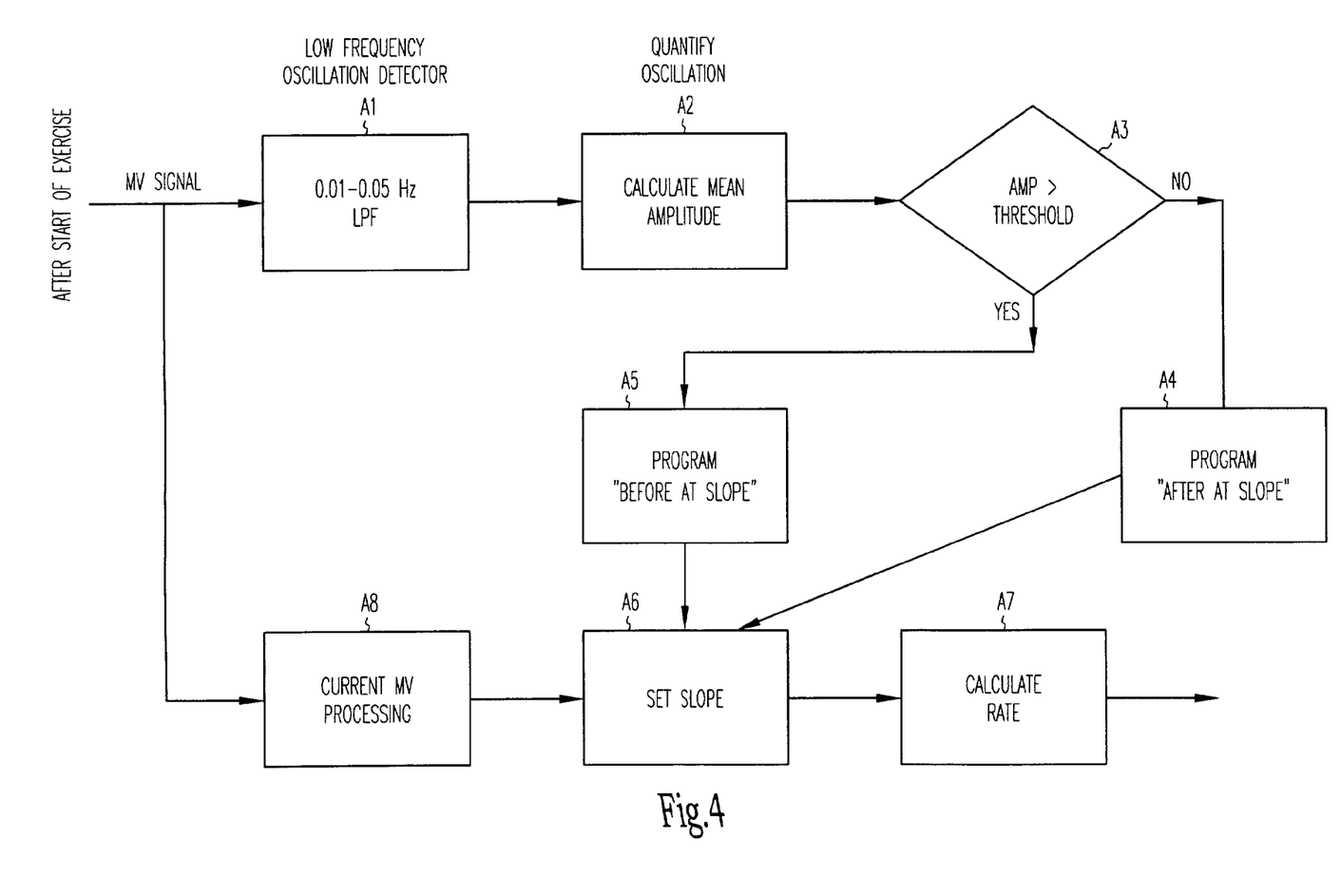
FIG. 4 is a flow diagram illustrating a particular implementation of the present method for adjusting the breakpoint of a dual-slope rate response curve.

One embodiment of the present invention involves the automatic setting of the rate-response curve breakpoint at the anaerobic threshold as determined by the point at which an oscillatory minute ventilation pattern disappears when a patient exercises with increasing intensity. The embodiment comprises: 1) measuring minute ventilation values and determining that an average of those minute ventilation values are increasing, signifying that the patient's exertion level is increasing; 2) determining an amplitude of an oscillatory component in the measured minute ventilation values to be above a specified threshold value; and, 3) if the amplitude of the oscillatory component falls below the specified threshold value as the average minute ventilation continues to increase, setting the breakpoint of the rate response curve equal to the presently measured minute ventilation value. FIG. 4 illustrates an exemplary implementation of the method. At step A1, the minute ventilation signal MV is input to a bandpass filter that extracts the frequency components of the signal that are between approximately 0.01 and 0.05 Hz. This corresponds to the frequency of oscillations in minute ventilation that have been found to occur in heart failure patients. At step A2, the mean amplitude of the extracted frequency components are calculated, and this value is compared to a specified threshold value at step A3. If the amplitude of the oscillations is below the threshold, the slope of the rate-response curve is programmed at step A4 to a value corresponding to what is appropriate when the patient is exercising above the anaerobic threshold. If the amplitude of the oscillations is above the threshold, the slope of the rate-response curve is set to a value appropriate for exercise below the anaerobic threshold at step A5. The sensor-indicated rate is calculated by processing the MV signal at step A8, setting the slope of the rate-response curve at step A6 in accordance with the results of either step A5 or step A4, and mapping of the minute ventilation to a sensor-indicated rate at step A7.

In another embodiment of the invention, an activity level measurement taken with a motion or pressure sensor such as an accelerometer is associated with a simultaneously taken minute ventilation measurement. The minute ventilation measurement is then cross-checked with the associated activity level measurement to ascertain if the minute ventilation measurement if reflective of the patient's true exertion level or is a result of the patient's oscillatory minute ventilation pattern. A mapping based upon either population data or an assessment of the individual patient may be used that relates a particular activity level to a particular percentage of the patient's minute ventilation reserve. The minute ventilation reserve is defined as the difference between the patient's maximum minute ventilation level and the minute ventilation level corresponding to rest. For example, a linear mapping may be used with a no-activity measurement value mapped to 0 percent of the reserve (i.e., the resting exertion level), a maximum activity measurement value mapped to 100 percent of the reserve (i.e., the maximum exercise capacity), and linearly interpolated values therebetween. Such a mapping thus allows a direct comparison between a minute ventilation measurement and a corresponding activity level measurement. Alternatively, ranges of minute ventilation values may be associated with particular ranges of activity levels to allow cross-checking of minute ventilation measurements.

6. Evaluation and Adjustment of Resynchonization Therapy

As aforesaid, it has been found that effective resynchronization therapy reduces the magnitude of the oscillatory minute ventilation pattern in heart failure patients. Accordingly, another embodiment of the invention involves the monitoring of minute ventilation oscillations so that the effectiveness of resynchronization pacing can be evaluated. Such information can be used by a clinician to then adjust various resynchronization pacing parameters. Alternatively, such parameters can be adjusted automatically by the device controller based upon which resynchronization pacing modes result in the greatest decrease in oscillatory minute ventilation. Such parameters may include, for example, the pacing configuration (i.e., which of the available pacing channels are used for pacing), the AV interval in atrial tracking and/or atrio-ventricular sequential pacing modes, the biventricular offset interval in biventricular pacing modes, as well as rate-adaptive pacing parameters as described above.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for adjusting the responsiveness of a rate-adaptive pacemaker operating in a patient, wherein measured minute ventilation values in the patient are mapped to a pacing rate by a dual-slope rate response curve, comprising:

measuring minute ventilation values and determining that an average of those minute ventilation values are increasing, signifying that the patient's exertion level is increasing;

determining an amplitude of an oscillatory component in the measured minute ventilation values to be above a specified threshold value; and, if the amplitude of the oscillatory component falls below the specified threshold value as the average minute ventilation continues to increase, setting the breakpoint of the rate response curve equal to the presently measured minute ventilation value.

2. The method of claim 1 wherein the measured minute ventilation values are passed through a high pass filter to determine the oscillatory component.

3. The method of claim 2 wherein the oscillatory component is in an approximate frequency range between 0.01 and 0.05 Hz.

4. The method of claim 1 further comprising:

measuring an activity level of the patient;

if the amplitude of the oscillatory component is below the specified threshold value, adjusting the pacing rate in accordance with the measured minute ventilation value and rate-response curve; and, if the amplitude of the oscillatory component is above the specified threshold, cross-checking the measured minute ventilation value with a measured activity level before adjusting the pacing rate.

5. The method of claim 1 further comprising pacing one or both ventricles in a ventricular resynchronization pacing mode.

6. The method of claim 5 further comprising transmitting an indication of the amplitude of the oscillatory component to an external programmer.

7. The method of claim 5 further comprising adjusting an operating parameter of the pacemaker if the amplitude of the oscillatory component in the measured minute ventilation values is above a specified threshold value.

8. The method of claim 7 wherein the adjusted operating parameter is an atrio-ventricular interval.

9. The method of claim 7 wherein the adjusted operating parameter is a biventricular offset interval.

10. A rate-adaptive pacemaker, comprising;

sensing and pacing channels for sensing cardiac depolarizations and delivering paces to a selected chamber;

a minute ventilation sensor, a controller for controlling the delivery of paces in accordance with a pacing mode at a programmed pacing rate, wherein measured minute ventilation values in the patient are mapped to a pacing rate by a dual-slope rate response curve;

wherein the controller is configured to determine if an amplitude of an oscillatory component in the measured minute ventilation values is above a specified threshold value and, if the amplitude of the oscillatory component falls below the specified threshold value as an average minute ventilation continues to increase, to set the breakpoint of the rate response curve equal to the presently measured minute ventilation value.

11. The pacemaker of claim 10 further comprising a bandpass filter for extracting the oscillatory component from the measured minute ventilation values.

12. The pacemaker of claim 10 wherein the filter has a passband in an approximate frequency range between 0.01 and 0.05 Hz.

13. The pacemaker of claim 10 wherein the controller is further programmed to adjust the pacing rate in accordance with the measured minute ventilation value and rate-response curve if the amplitude of the oscillatory component is below the specified threshold value, and, if the amplitude of the oscillatory component is above the specified threshold, to cross-check the measured minute ventilation value with a measured activity level before adjusting the pacing rate.

14. The pacemaker of claim 10 wherein the controller is programmed to pace one or both ventricles in a ventricular resynchronization pacing mode.

15. The pacemaker of claim 14 further comprising a telemetry interface for transmitting an indication of the amplitude of the oscillatory component to an external programmer.

16. The pacemaker of claim 14 wherein the controller is configured to adjust an operating parameter of the pacemaker if the amplitude of the oscillatory component in the measured minute ventilation values is above a specified threshold value.

17. The pacemaker of claim 16 wherein the operating parameter adjusted by the controller is an atrio-ventricular interval.

18. The pacemaker of claim 16 wherein the operating parameter adjusted by the controller is a biventricular offset interval.

19. The pacemaker of claim 16 wherein the operating parameter adjusted by the controller is a pacing configuration that determines which pacing channels are to be used for pacing.

20. The pacemaker of claim 16 wherein the operating parameter adjusted by the controller is a rate-adaptive pacing parameter.

* * * * *